United States Patent
Brown et al.

(10) Patent No.: US 11,419,892 B2
(45) Date of Patent: Aug. 23, 2022

(54) ANTIMICROBIAL PLATELET-LIKE PARTICLES

(71) Applicant: NORTH CAROLINA STATE UNIVERSITY, Raleigh, NC (US)

(72) Inventors: Ashley Brown, Raleigh, NC (US); Erin Sproul, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 4 days.

(21) Appl. No.: 16/966,646

(22) PCT Filed: Feb. 1, 2019

(86) PCT No.: PCT/US2019/016232
§ 371 (c)(1),
(2) Date: Jul. 31, 2020

(87) PCT Pub. No.: WO2019/152766
PCT Pub. Date: Aug. 8, 2019

(65) Prior Publication Data
US 2020/0352990 A1 Nov. 12, 2020

Related U.S. Application Data

(60) Provisional application No. 62/625,020, filed on Feb. 1, 2018.

(51) Int. Cl.
*A61K 33/242* (2019.01)
*A61K 47/58* (2017.01)
(Continued)

(52) U.S. Cl.
CPC .......... *A61K 33/242* (2019.01); *A61K 33/38* (2013.01); *A61K 47/58* (2017.08); *A61K 47/6843* (2017.08); *A61K 47/6927* (2017.08)

(58) Field of Classification Search
CPC .................................................. A61K 33/242
See application file for complete search history.

(56) References Cited

U.S. PATENT DOCUMENTS

2006/0233854 A1  10/2006  Seliktar et al.
2016/0271292 A1   9/2016  Barker et al.
(Continued)

FOREIGN PATENT DOCUMENTS

WO    2019/094526 A1    5/2016
WO    2018/015976 A1    1/2018
WO  WO-2018015976 A1 *  1/2018  .......... A61K 31/661

OTHER PUBLICATIONS

Brown et al. (Ultrasoft microgels displaying emergent platelet-like behaviours, Nature Materials, 2015, p. 2) (Year: 2015).*
(Continued)

*Primary Examiner* — Benjamin J Packard
(74) *Attorney, Agent, or Firm* — Meunier Carlin & Curfman LLC

(57) ABSTRACT

Disclosed herein are platelet-like particles incorporating antimicrobial metallic nanoparticles. The platelet-like particles include an ultra-low crosslinked polymeric microgel and fibrin targeting moiety. The antimicrobial metallic nanoparticles can be covalently or noncovalently incorporated into the platelet-like particles. The particles are useful to stop bleeding and to promote wound healing while at the same time suppressing bacterial infections that can accompany tissue damage.

20 Claims, 6 Drawing Sheets

(51) Int. Cl.
*A61K 47/68* (2017.01)
*A61K 47/69* (2017.01)
*A61K 33/38* (2006.01)

(56) References Cited

U.S. PATENT DOCUMENTS

2017/0340771 A1  11/2017  Castro Feo et al.
2018/0200404 A1  7/2018  Aper et al.

OTHER PUBLICATIONS

International Search Report and Written Opinion issued in corresponding application No. PCT/US2019/016232, dated Mar. 27, 2019, 8 pages.
Brown, AC et al., Ultrasoft microgels displaying emergent, platelet-like, behaviors; Nature Materials; Jun. 1, 2015; p. 2.
International Search Report and Written Opinion issued in application No. PCT/US2020/062580, dated Feb. 19, 2021, 9 pages.
Extended European Search Report issued for European Application No. 19746617, dated Sep. 28, 2021.
Liu, Yun-Yun, et al. "Investigation of Ag nanoparticles loading temperature responsive hybrid microgels and their temperature controlled catalytic activity." Colloids and Surfaces A: Physicochemical and Engineering Aspects 393 (2012): 105-110.
Han, De-Man, Qiang Matthew Zhang, and Michael J. Serpe. "Poly (N-isopropylacrylamide)-co-(acrylic acid) microgel/Ag nanoparticle hybrids for the colorimetric sensing of $H_2O_2$." Nanoscale 7.6 (2015): 2784-2789.

\* cited by examiner

US 11,419,892 B2

ANTIMICROBIAL PLATELET-LIKE PARTICLES

CROSS-REFERENCE TO RELATED APPLICATION

This application is a national stage application filed under 35 U.S.C. § 371 of PCT/US2019/016232 filed on Feb. 1, 2019, which claims the benefit of U.S. Provisional Application 62/625,020, filed Feb. 1, 2018, and entitled "ANTIMICROBIAL PLATELET-LIKE PARTICLES," the contents of which are hereby incorporated in their entireties.

FIELD OF THE INVENTION

The invention is directed to platelet-like particles containing antimicrobial metallic nanoparticles.

BACKGROUND

Traumatic hemorrhage remains a significant clinical problem despite decades of research. According to the CDC, injury is the leading cause of death for men and women between the ages of 1 and 44, and many trauma victims often exsanguinate before reaching the hospital. Even in patients where hemostasis is achieved, subsequent wound repair can be impeded by several complicating factors including an increased risk of infection which can be fatal. Therefore, a critical need exists to develop new therapies to treat the wounds of trauma victims to prevent hemorrhaging and subsequent infection. The current clinical treatments for bleeding are mechanical hemostatic agents such as gelatin & collagen sponges, active hemostatic agent such as thrombin, flowable hemostatic agents and fibrin sealants. While these materials are effective for treating smaller wounds, they are limited at treating massive hemorrhaging. Additionally, all of these materials are applied topically and cannot be used to treat internal bleeding. These limitations motivate the need to develop therapeutics to treat hemorrhaging and target internal bleeding.

In the body coagulation occurs in response to injury in order to stop bleeding by forming platelet-rich fibrin clots Immediately following injury platelets are activated, aggregate, and augment fibrin formation. Platelets bind fibrin fibers through $\alpha_{IIb}\beta_3$ integrins. These interactions crosslink and stabilize the developing clot thus increasing matrix stiffness which is a central cue to orchestrating wound healing events. Platelets then spread within the fibrin network and actively modify network properties over time by retracting the clot and thereby increasing fibrin density. Clot formation is an essential first step for achieving cessation of bleeding and involves the formation of a platelet plug embedded within a fibrin mesh. Over time, platelets contract the fibrin clot, which stabilizes the network and contributes to enhanced wound healing outcomes.

There has been recent interest in mimicking the biological properties of platelets with synthetic particles. These typically comprise a nanoparticle platform such as red blood cells (RBCs), albumin particles, liposomes, latex beads that are surface-decorated with peptides or ligands. These particles recreate specific biological characteristics of platelets, including targeting of wound and disease sites and facilitating platelet aggregation. Notable examples include synthetic platelets composed of PLGA-PLL core with PEG arms terminated with RGD moieties were found to bind platelets and promote platelet aggregation. Additionally, liposomes decorated with vWF and collagen binding motifs have been shown to mimic the adhesion mechanisms of platelets to the wound site under flow. Other efforts in synthetic platelet design have focused on matching platelet shape and mechanics to recreate the marginalization. Others have explored deformable particles with platelet-like discoid morphology, for example a nanocomposite hydrogel containing gelatin and silicate nanoplatelets that occluded blood flow in arteries and veins in mice and pig.

Platelet-like particles have been previously evaluated for effectiveness in clotting. Recently developed platelet-like-particles (PLPs) have been shown to recapitulate key functions of endogenous platelets, including augmentation of clotting of adult plasma in vitro, decreased bleeding times in vivo in rodent models of traumatic injury, specific homing to injury sites, and clot retraction. Clot retraction is an important feature for clot stability and wound repair. The clot retraction feature of PLPs is the result of the high degree of microgel deformability and high fibrin-binding ability imparted by a fibrin binding antibody.

There remains a need for additional compositions that can promote wound healing as well as suppress microbial infections. There remains a need for biocompatible compositions that can be used to treat internal injuries.

SUMMARY

Disclosed herein are platelet-like particles incorporating antimicrobial metallic nanoparticles. The platelet-like particles include an ultra-low crosslinked polymeric microgel and a fibrin targeting moiety. The antimicrobial metallic nanoparticles can be covalently or noncovalently incorporated into the platelet-like particles. The particles are useful to promote clotting and subsequent wound healing while at the same time suppressing bacterial infections that can accompany tissue damage. The details of one or more embodiments are set forth in the descriptions below. Other features, objects, and advantages will be apparent from the description and from the claims.

DETAILED DESCRIPTION

Figure 1:
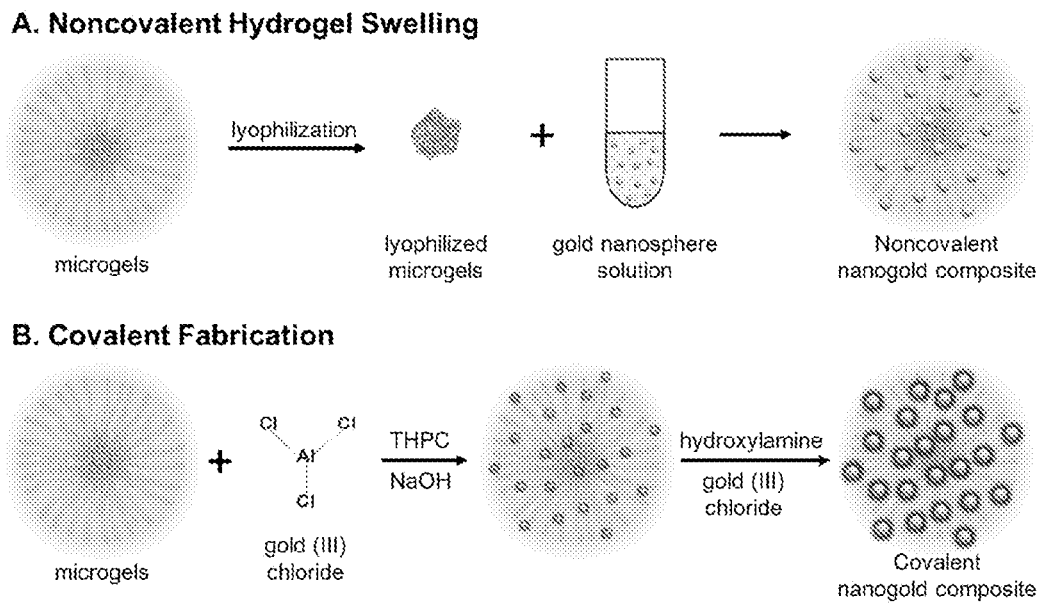
FIG. 1: Microgels containing gold were formed through noncovalent and covalent methods to obtain nanogold composites (NGCs). In the noncovalent fabrication method, A, lyophilized microgels are rehydrated with solution containing gold nanospheres. B, Covalent NGCs are formed in a 2-step process to seed gold (III) chloride and then grow gold into larger size nanoparticles.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Disclosed herein are highly deformable microgels that function like platelets in vivo. The microgels include at least one ultra-low crosslinked polymer, fibrin-binding moiety, and antimicrobial metallic nanoparticle. Suitable ultra-low crosslinked polymers include polyacrylamides, polyacrylates, poly(acrylic acids), polyethylene glycols, polyvinyl alcohols, polysaccharides, polyvinylpyrrolidones, and copolymers thereof. When the ultra-low crosslinked polymer is a copolymer, it can be a random copolymer or block copolymer. The ultra-low crosslinked polymers are characterized by a low degree of crosslinking in the polymer network. For instance, the crosslinking density can be no greater than 2.5%, no greater than 2.0%, no greater than 1.5%, no greater than 1.0%, no greater than 0.75%, no greater than 0.50%, no greater than 0.25%, no greater than 0.10%, or no greater than 0.05%.

Unless stated to the contrary, the term "polyacrylamide" includes the unsubstituted polyacrylamide polymer as well as poly(N-alkylacrylamides) and poly(N,N-dialkylacrylamides). The N-alkylacrylamide can be an N—$C_1$-$C_4$alkylacrylamide, the N,N-dialkylacrylamide can be an N,N-di($C_1$-$C_4$)alkylacrylamide. The alkyl groups in in the N,N-dialkylacrylamides can be the same, or can be different. The ultra-low crosslinked polymer can be derived from one or more monomers such as methylacrylamide, ethylacrylamide, n-propylacrylamide, iso-propylacrylamide, n-butylacrylamide, iso-butylacrylamide, sec-butylacrylamide, tert-butylacrylamide, dimethylacrylamide, diethylacrylamide, di-n-propylacrylamide, di-iso-propylacrylamide, N-methyl-N-ethylacrylamide, N-methyl-N-n-propylacrylamide, N-ethyl-N-n-propylacrylamide, N-methyl-N-iso-propylacrylamide, and N-ethyl-N-iso-propylacrylamide. In some instances, the ultra-low crosslinked polymer is derived from monomers including N-isopropylacrylamide, N-isopropylmethacrylamide, N,N-diethylacrylamide, or a copolymer thereof.

In certain embodiments, the ultra-low crosslinked polymer can be a copolymer of one or more polyacrylamides (as defined above) and acrylic acid. Generally, such copolymers can be prepared from a precipitation polymerization reaction of a mixture of acrylic acid and suitable acrylamide monomers. The acrylic acid component can be present in an amount of no more than 40%, no more than 30%, no more than 20%, no more than 10%, no more than 9%, no more than 8%, no more than 7%, no more than 6%, no more than 5%, no more than 4%, no more than 3%, no more than 2%, or no more than 1% by weight of the total monomer mixture. The precipitation polymerization may be carried out using a free radical initiator such as ammonium persulfate (APS) or 2,2'-azobis(amidinopropane)dihydrochloride.

The precipitation reaction can be carried out in the absence of any exogenous crosslinking agent. In such cases, crosslinking takes place via chain-transfer mechanisms. Such processes are designated self-crosslinking reactions, producing self-crosslinked polymers. In other instance, the precipitation may be carried out using an exogenous crosslinking agent, for instance polyfunctional acrylates and polyfunctional acrylamides such as N,N'-methylenebis (acrylamide), N,N-(1,2-dihydroxyethylene)bisacrylamide, ethylene glycol diacrylate, di(ethylene gycol) diacrylate, tetra(ethylene glycol) diacrylate, ethylene glycol dimethacrylate, di(ethylene glycol) dimethacrylate, and tri(ethylene glycol) dimethacrylate.

The ultra-low crosslinked polymer can have a hydrodynamic radius, in the collapsed state, from 0.05-20 μm, from 0.05-15 μm, from 0.05-10 μm, from 0.1-10 μm, from 0.2-10 μm, from 0.5-10 μm, from 1-10 μm, from 2-10 μm, from 5-10 μm, from 0.2-8 μm, from 0.2-6 μm, from 0.2-4 μm, from 0.2-2 μm, from 0.2-1 μm, from 0.5-8 μm, from 0.5-6 μm, from 0.5-4 μm, or from 0.5-2 μm.

The microgels disclosed herein can have a volume in the hydrated state that is between 0.05-50 $\mu m^3$, between 0.05-25 $\mu m^3$, between 0.05-10 $\mu m^3$, between 0.05-5 $\mu m^3$, between 0.1-5 $\mu m^3$, between 0.1-2.5 $\mu m^3$, between 0.1-2 $\mu m^3$, between 0.1-1.5 $\mu m^3$, between 0.1-1 $\mu m^3$, between 0.25-1 $\mu m^3$, or between 0.25-0.75 $\mu m^3$.

The microgels disclosed herein are highly deformable. For instance, in the collapsed state the microgel deforms such that the microgel spread diameter is at least 10×, at least 15×, at least 20×, at least 25×, at least 30×, at least 40×, at least 50×, at least 100×, at least 250×, at least 500×, at least 750×, or at least 1,000× the height of the microgel. In some embodiments, in the collapsed state the microgel deforms such that the microgel spread diameter is from 10×-1,000×, from 25×-1,000×, from 50×-1,000×, from 100×-1,000×, from 250×-1,000×, or from 500×-1,000× the height of the microgel.

The deformable microgels also include at least one fibrin binding moiety, for instance fibrin-binding IgG antibodies, fibrin-binding peptides (fibrin knob mimics), Fragment-D binding antibodies, as well as other antibody fragments than bind fibrin. Exemplary fibrin binding moieties are disclosed in U.S. Publication 2016/0271292 at ¶¶[0050-0057]. Fibrin binding moieties may be conjugated to the ultra-low crosslinked polymer using conventional techniques, for instance using standard EDC/NHS chemistry.

The microgels disclosed herein include antimicrobial metallic nanoparticles. Suitable antimicrobial metallic nanoparticles include gold nanoparticles, silver nanoparticles, copper nanoparticles, aluminum nanoparticles, zinc nanoparticles, and mixtures thereof. The anti-microbial metallic nanoparticles can have an average particle size no greater than 1,000 nm, no greater than 750 nm, no greater than 500 nm, no greater than 250 nm, no greater than 100 nm, no greater than 75 nm, no greater than 50 nm, no greater than 25 nm, no greater than 15 nm, no greater than 10 nm, no greater than 5 nm, no greater than 2.5 nm, or no greater than 1.0 nm. In some embodiments, the anti-microbial metallic nanoparticles can have an average particle size from 1.0-1,000 nm, from 1.0-750 nm, from 1.0-500 nm, from 1.0-250 nm, from 1.0-100 nm, from 1.0-75 nm, from 1.0-50 nm, from 1.0-n 25 nm, from 1.0-15 nm, from 1.0-10 nm, from 1.0-5 nm, from 1.0-2.5 nm, from 5-200 nm, from 10-200 nm, from 15-200 nm, from 25-200 nm, from 50-200 nm, from 75-200 nm, or from 100-200 nm.

The microgels can include antimicrobial metallic nanoparticles at a variety of different loadings. In some instances, the anti-microbial metallic nanoparticles are present in an amount, per gram of microgel, at least 5 ng, at least 10 ng, at least 20 ng, at least 25 ng, at least 50 ng, at least 100 ng, at least 250 ng, at least 500 ng, at least 750 ng, at least 1,000 ng, at least 2,500 ng, at least 5,000 ng, at least 7,500 ng, or at least 10,000 ng. In some embodiments, the anti-microbial metallic nanoparticles are present in an amount, per gram of microgel, from 5-10,000 ng, from 5-5,000 nm, from 5-2,500 ng, from 5-1,000 ng, from 5-500 ng, from 5-250 ng, from 5-100 ng, from 5-50 ng, from 5-25 ng, from 100-2,500 ng, from 500-2,500 ng, from 1,000-2,500 ng, from 2,500-10,000 ng, or from 5,000-10,000 ng.

In certain embodiments, the amount of antimicrobial metallic nanoparticles (NP) in the microgel can be characterized by the number of nanoparticles per unit volume microgel. For instance, the antimicrobial metallic nanoparticles can be present in an amount between 1-1,000 nanoparticles per $\mu m^3$ microgel (i.e., 1-1,000 np/$\mu m^3$), between 25-1,000 np/$\mu m^3$, between 50-1,000 np/$\mu m^3$, between 75-1,000 np/$\mu m^3$, between 100-1,000 np/$\mu m^3$, between 250-1,000 np/$\mu m^3$, between 500-1,000 np/$\mu m^3$, between 750-1,000 np/$\mu m^3$, between 25-100 np/$\mu m^3$, between 100-250 np/$\mu m^3$, between 250-500 np/$\mu m^3$, between 500-750 np/$\mu m^3$, between 250-750 np/$\mu m^3$, between 1-100 np/$\mu m^3$, between 25-250 np/$\mu m^3$, or between 25-500 np/$\mu m^3$.

The microgels disclosed herein may be obtained by incorporating antimicrobial metallic nanoparticles into an ultra-low crosslinked polymer, and conjugation of a fibrin binding moiety to the ultra-low crosslinked polymer. In some instances, the antimicrobial metallic nanoparticles are incorporated prior to conjugation of the fibrin binding moiety, whereas in others the antimicrobial metallic nanoparticles are incorporated subsequent to conjugation of the fibrin binding moiety.

The incorporation of the antimicrobial metallic nanoparticles can be achieved through covalent or noncovalent means. To obtain noncovalent incorporation, a dried ultra-low crosslinked microgel (which may or may not be conjugated to a fibrin binding moiety) can be swelled in an aqueous composition that includes antimicrobial metallic nanoparticles. The aqueous composition includes the antimicrobial metallic nanoparticles in a concentration of at least 0.01 mg/ml, at least 0.02 mg/ml, at least 0.03 mg/ml, at least 0.04 mg/ml, at least 0.05 mg/ml, at least 0.06 mg/ml, at least 0.7 mg/ml, at least 0.08 mg/ml, at least 0.09 mg/ml, at least 0.1 mg/ml, at least 0.25 mg/ml, at least 0.50 mg/ml, at least 0.75 mg/ml, or at least 1.0 mg/ml. In some embodiments, the aqueous composition includes the antimicrobial metallic nanoparticles in a concentration from 0.01-1 mg/ml, from 0.02-1 mg/ml, from 0.05-1 mg/ml, from 0.1-1 mg/ml, from 0.25-1 mg/ml, from 0.5-1 mg/ml, from 0.75-1 mg/ml, from 0.02-0.25 mg/ml, from 0.02-0.1 mg/ml, from 0.1-0.5 mg/ml, or from 0.1-0.25 mg/ml.

Covalent incorporation of antimicrobial metallic nanoparticles may be achieved by reducing an appropriate metal salt in the presence of a dried ultra-low crosslinked polymer (which may or may not be conjugated to a fibrin binding moiety). Suitable metal salts include $Au^{1+}$, $Au^{3+}$, $Ag^{1+}$, $Cu^{1+}$, $Cu^{2+}$, $Cu^{3+}$, $Zn^{2+}$, and $Al^{3+}$ salts. Mixtures of two or more different metal salts may be used, which can yield mixed metal nanoparticles, e.g., Zn/Ag.

In a first aspect of the invention there is provided a method of promoting wound healing in a subject comprising administering to the subject, the microgels disclosed herein.

The wound to be healed may be present in any organ or tissue, including internal organs or tissues or external tissues, such as skin. The wound may be the result of an injury, bite or burn. The organ or tissue may be any one or more of skin, muscle, liver, kidneys, lungs, heart, pancreas, spleen, stomach, intestines bladder, ovaries, testicles, uterus, cartilage, tendon, ligament, bone and the like. In particular embodiments, the wound is in the skin and/or muscle.

In some embodiments, the microgel is administered soon after the wound is incurred. In other embodiments, the wound is a chronic wound that has failed to heal over days, weeks, months or years. In yet other embodiments, the wound is an existing wound which has failed to heal at a normal rate or has failed to respond to other therapies.

As used herein, the term "wound" refers to physical disruption of the continuity or integrity of tissue structure. Wounds may be acute or chronic and include cuts and lacerations, surgical incisions or wounds, punctures, grazes, scratches, compression wounds, abrasions, friction wounds, decubitus ulcers (e.g. pressure or bed sores); thermal effect wounds (burns from cold and heat sources), chemical wounds (e.g. acid or alkali burns) or pathogenic infections (e.g. viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, eg psoriasis and eczema, stomach or intestinal ulcers, oral wounds, including a ulcers of the mouth, damaged cartilage or bone, amputation wounds and corneal lesions.

As used herein, the term "chronic wound" refers to a wound that has not healed within a normal time period for healing in an otherwise healthy subject. Chronic wounds may be those that do not heal because of the health of the subject, for example, where the subject has poor circulation or a disease such as diabetes, or where the subject is on a medication that inhibits the normal healing process. Healing may also be impaired by the presence of infection, such as a bacterial, fungal or parasitic infection. In some instances, a chronic wound may remain unhealed for weeks, months or even years. Examples of chronic wounds include but are not limited to, diabetic ulcers, pressure sores and tropical ulcers (i.e., jungle rot).

The microgels of the invention may also be applied to a wound which is healing or has healed with excessive scarring. Examples of such wounds are those that are producing or have produced keloid scars or hypertrophic scars.

In some embodiments, the wound is infected with a bacterial infection. The bacterial infection may be caused by a Gram positive or Grain negative bacteria, especially a Gram positive bacteria. Non-limiting examples of bacteria that are controlled by the microgels of the invention include bacteria of the Genus *Bacillus*, such as *B. subtilis*, *B. anthracis*, *B. cereus*, *B. firmis*, *B. lichenifomis*, *B. megaterium*, *B. punilus*, *B. coagulans*, *B. pantothenticus*, *B. alvei*, *B. brevis*, *B. circubins*, *B*, *laterosporas*, *B. macerans*, *B. polymyxa*, *B. stearothermophilus*, *B. thuringieusis* and *B. sphaericus*; *Staphylococcus* such as *S. aureus*, *S. epidermidis*, *S. haemolyticus*, *S. saprophyticus*; *Streptococcus*, for example, *S. pyrogenes*, *S. pneumoniae*, *S. alagactiae*, *S. dysgalactiae*, *S. equisimilis*, *S. equi*, *S. zooepiaemicus*, *S. anginosus*, *S. salwarius*, *S. millera*, *S. sanguis*, *S. mitior, S. mutans*, *S. faecalis*, *S. faecium*, *S, bovis*, *S. equinus*, *S. uberus* and *S. avium*; *Aerococcus* spp., *Gemella* spp., *Corynebacterium* spp., *Listeria* spp., *Kurthia* spp., *Lactobacillus* spp., *Erysipelothrix* spp., *Arachnia* spp., *Actinomyces* spp., *Propionibacterium* spp., *Rothia* spp, *Bifidobacterium* spp., *Clostridium* spp., *Eubacterium* spp., *Serratia* spp., *Klebsiella* spp., *Proteus* spp., *Enterococcus* spp., *Pseudomonas* spp., *Nocardia* spp. and *Mycobacterium* spp.

In some embodiments, the wound is infected with a fungal infection. The fungal infection may be caused by filamentous fungi or yeasts. Non-limiting examples of fungi that are controlled by the microgel include fungi of the Genus such as *Aspergillus* spp., *Mucor* spp., *Trichtophyton* spp., *Cladosporium* spp., *Ulocladium* spp., *Curvularia* spp., *Aureobasidium* spp., *Candida albicans*, *Candida* spp., *Cryptococcus* spp., *Malessezia pachydermatis*, *Malessezia* spp. and *Trichosporon* spp.

In some embodiments, the wound is infected by both bacterial and fungal infections, including in biofilms.

The microgels can be used advantageously in a wide variety of wound healing contexts, using a variety of different compositions for application to a wound site. For instance, the microgels may be used with a wound dressing which can be directly contacted with a wound. The microgels can be impregnated in a wound dressing or coated on the wound dressing using conventional techniques. The wound dressing can be made of a fibrin gel. The wound dressing can also be made of absorbent materials such as cotton of fleece. The wound dressing can also be made of synthetic fibers for example polyamide fibers. In certain embodiments, the wound dressing can have multiple layers including an adhesive layer, an absorbent layer, and moisture regulation layer. In other embodiments, the microgel may be dispersed in a solution for injection, either intravenous, intraperitoneal, or directly injected into the would area. In further embodiments, the microgel may be lyophilized and mixed with one or more pharmaceutical carriers, and formulated into ointments, lotions, creams, gels, drops, suppositories, sprays, liquids and powders.

The disclosed microgels can be used as a sealant or tissue adhesive to seal ruptures or open wounds by promoting blood clotting. The microgels can be formulated as a dry powder or aqueous suspension and packaged into discrete packets or units to form a kit. Surgical hemostatic agents and sealants including the disclosed microgels may be used as an aid to cease hemorrhage during surgery, either mechanically or by augmenting the body's response to coagulation.

While the microgels may be administered neat, it may be more convenient to administer the microgels in the form of a pharmaceutical composition together with a pharmaceutically acceptable carrier, diluent and/or excipient.

Dosage form and rates for pharmaceutical use and compositions are readily determinable by a person of skill in the art.

Dosage forms include tablets, dispersions, suspensions, injections, solutions, syrups, troches, capsules, suppositories, aerosols, transdermal patches, impregnated (occlusive) dressing, creams, gels and the like. These dosage forms may also include injecting or implanting devices designed specifically for, or modified to, controlled release of the microgel. Controlled release of the microgel may be effected by coating the same, for example, with hydrophobic polymers including acrylic resins, waxes, higher aliphatic alcohols, polyactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers and acceptable carriers for systemic administration may also be incorporated into the compositions of this invention.

Suitably, the pharmaceutical composition includes at least one pharmaceutically acceptable excipient or an acceptable excipient. By "pharmaceutically acceptable excipient" is meant a solid or liquid filler, diluent or encapsulating substance that may be safely used. Depending upon the particular route of administration, a variety of carriers, well known in the art may be used. These carriers or excipients may be selected from a group including sugars, starches, cellulose and its derivates, malt, gelatin or other gelling agents, talc, calcium sulphate, vegetable oils, synthetic oils, alcohols and/or polyols, alginic acid, phosphate buffered solutions, emulsifiers, isotonic saline, and pyrogen-free water.

Any suitable route of administration may be employed for providing a human or non-human patient with the pharmaceutical composition. For example, oral, topical, rectal, parenteral, sublingual, buccal, intravenous, intraarticular, intra-muscular, intra-dermal, subcutaneous, inhalational, intraocular, intraperitoneal, intracerebroventricular, transdermal and the like may be employed.

Pharmaceutical compositions suitable for administration may be presented in discrete units such as syringes, vials, tubes, capsules, sachets or tablets each containing a predetermined amount of microgel, as a powder or granules or as a solution or a suspension in an aqueous liquid, a cyclodextrin solution, a non-aqueous liquid, an oil-in-water emulsion or a water-in-oil emulsion or as a solution or suspension in a cream or gel or as a suspension of microgel, including but not limited to silica or polylactide micro- or nano-particles. Such compositions may be prepared by any of the method of pharmacy but all methods include the step of bringing into association one or more microgel with the carrier which constitutes one or more necessary ingredients. In general, the compositions are prepared by uniformly and intimately admixing the microgel with liquid carriers or finely divided solid carriers or both, and then, if necessary, shaping the product in to the desired presentation.

In powders, the carrier is a finely divided solid which is in a mixture with the microgel.

In tablets, the microgel is mixed with the carrier having the necessary binding capacity in suitable proportions and compacted in the shape and size desired.

Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the microgel with encapsulating material as carrier providing a capsule in which the microgel, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the microgel is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the microgel such carriers as are known in the art to be appropriate.

Liquid form preparations include solutions, suspensions, and emulsions, for example, water or water-propylene glycol solutions. For example, parenteral injection liquid preparations can be formulated as solutions in aqueous 1,2-propanediol, dimethylsulfoxide (DMSO), aqueous solutions of gamma cyclodextrin or 2-hydroxypropyl-beta-cyclodextrin, saline solution or polyethylene glycol solution, with or without buffer.

The microgels according to the present invention may thus be formulated for parenteral administration (e.g. by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, and may contain formulatory agents such as suspending, stabilizing and/or dispersing agents. Alternatively, the microgel may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the microgel in water and adding suitable colorants, flavors, stabilizing and thickening agents, as desired.

Aqueous suspensions suitable for oral use can be made by dispersing the microgel in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the microgel, colorants, flavors, stabilizers, buffers, artificial and natural sweeteners, dispersants, thickeners, solubilizing agents, and the like.

For topical administration to the epidermis or other organ, the microgels may be formulated as gels, ointments, emulsions, pastes, creams or lotions, as a transdermal patch, or as mixtures with fibrin gels. Gels may be prepared using suitable thickening agents and adding them to aqueous/alcoholic compositions of microgel. Suitable thickening or gelling agents are known in the art, such as the polyvinyl carboxy polymer, Carbomer 940. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration also include solutions or suspensions that may be administered topically in the form of a bath or soak solution or a spray.

These formulations may be suitably applied to combat skin irritations, insect bites and foot wounds.

Formulations suitable for topical administration in the mouth include lozenges comprising microgel in a flavored base, usually sucrose and acacia or tragacanth; pastilles comprising the microgel in an inert base such as gelatin and glycerin or sucrose and acacia; and mouthwashes comprising the microgel in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the microgel according to the invention may be encapsulated with cyclodextrins, or formulated with their agents expected to enhance delivery and retention in the nasal mucosa.

Administration to the respiratory tract may also be achieved by means of an aerosol formulation in which the microgel is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of microgel may be controlled by provision of a metered valve.

Alternatively, the microgel may be provided in the form of a dry powder, for example a powder mix of the microgel in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

EXAMPLES

The following examples are for the purpose of illustration of the invention only and are not intended to limit the scope of the present invention in any manner whatsoever.

Example 1: Ultra-Low Crosslinked Microgel (ULC) Synthesis

N-Isopropylacrylamide (NIPAm) (Sigma) was recrystallized with hexanes heated to 60° C. for 1 hr and 0.22 µm filtered after cooling. NIPAm (95% of a 140 mM monomer solution by weight) was dissolved completely with agitation (1 hr) then filtered in ultrapure water into a 3-neck reaction vessel heated in silicon oil, stirred at 450 rpm, and fluxed at 70° C. A condenser with running cold water was attached to the middle neck, nitrogen was bubbled through the monomer solution via a side neck, and a temperature probe connected to a hot plate through a feedback loop was in the $3^{rd}$ neck. NIPAm was fluxed 50 min before adding co-monomer Acrylic acid (AAc) (Sigma) (5% by weight) to flux an additional 10 minutes prior to initiation. The nitrogen was removed to add 1 mM ammonium persulfate (APS) to initiate the reaction and the nitrogen was then gently blown over the surface of the solution. The reaction proceeded for 6 hours, while stirring, with water flow through condenser. The reaction vessel was removed from the oil and stirred to cool overnight. Microgels were purified by filtering over glass wool to remove large aggregates and by dialysis to remove excess monomers in 1000 kDa MWCO cellulose ester dialysis tubing (spectrum) against ultrapure water (40× volume with 2 water changes over 48 hr).

Example 2: Nanogold Composite (NGC) Fabrication

Two methods of gold incorporation were performed to create gold-microgel composites; the first comprised of a noncovalent method and the second comprised of a covalent synthesis method. The noncovalent NGC synthesis method incorporates gold nanospheres into microgels via noncovalent swelling. Microgels were lyophilized and then rehydrated at a microgel concentration of 10 mg/mL with an aqueous suspension of gold nanospheres (5, 50 or 100 nm diameter) at a gold concentration of 0.05 mg/mL in 2 mM sodium citrate (nanoComposix, San Diego, Calif.) with shaking at room temperature overnight.

The second method of NGC fabrication involved a covalent nanogold composite fabrication method. In this method, gold-microgel composites were synthesized in a two-step procedure. In this method, THPC-mediated reduction of $HAuCl_4 \cdot 3H_2O$ was used to form small Au NPs (size<3 nm), which were then grown in size (~150 nm) using hydroxylamine and $Au^{3+}$ solution. The second step of the composite particle production process involves seeded growth of gold particles in order to covalently bond them within the microgel crosslinking network. An aqueous microgel suspension was made by stirring 5 mg purified microgels at 450 rpm in 4.21 mL ultrapure water at least 20 minutes. For experimental testing of particle properties, 3 different amounts of gold were incorporated into the particle. Gold (III) Chloride Hydrate solution (20 mM, 150 µL-450 µL) and 1M NaOH solution (50-150 µL) were added and the mixture was stirred at room temperature for 30 minutes to allow for adequate distribution of reaction components. To reduce the gold ions and covalently bond them within the microgel particle network, 2.45 µL-7.35 µL of tetra(hydroxymethyl) phosphonium chloride (THPC) was added. Following completion of this part of the reaction, centrifugation at 21,100 g for 20 minutes and resulting supernatant of the solution was taken out to remove any gold particles that were created but not incorporated into a microgel particle. The remaining gold-microgel solution was then resuspended into 10 mL ultrapure water before proceeding with the gold growth step of the reaction to increase the size of seeded gold nanoparticles. 50 µL-150 µL of 80 mM hydroxylamine was added immediately before 60 µL-180 µL 100 mM Gold (III) Chloride Hydrate solution in order to grow the sizes of the gold nanoparticles within the microgels. The particles were purified by centrifugation at 21,100 g for 20 minutes, removal of supernatant, washing with ultrapure water and centrifuging again before resuspension of pellet in ultrapure water to a desired concentration. The final product of this synthesis is a nanogold composite composed of pNIPAm/AAc microgels with covalently bound gold nanoparticles dispersed throughout.

Example 3: Production of Fibrin-Specific NCGs

Noncovalent nanogold composite platelet-like particles (ncNGC PLPs) were created by adding fibrin-binding antibody to microgels and subsequent swelling with gold nanosphere solution. A fibrin-binding IgG antibody (Sheep anti-human Fibrin fragment E, Affinity Biologicals, Ancaster, ON) was first conjugated to the acrylic acid residues of microgels through EDC/NHS coupling to create deformable fibrin-binding PLPs. Purification of PLPs was performed either by dialysis against 200× volume ultrapure water over 48 hours with 3 diluent exchanges or either by centrifuging at 10,000 rpm×30 min and washing 3 times with 30× volume ultrapure water. PLPs were lyophilized and loaded with gold by rehydration, described above. Covalent nanogold composites were modified to bind fibrin through similar EDC/NHS chemistry, but after covalent gold incorporation. cNGC PLPs were similarly purified by dialysis or centrifugation and washing.

Figure 2:
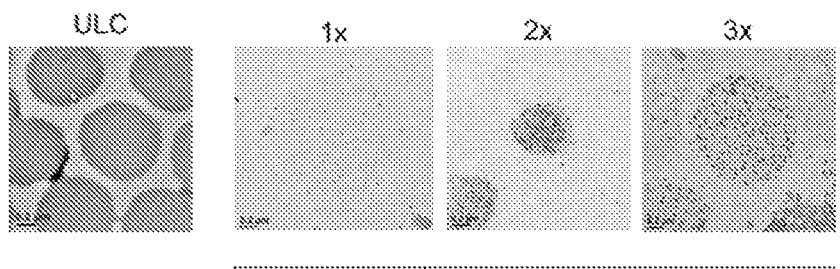
FIG. 2: Transmission Electron Microscopy demonstrated homogenous distribution of gold nanoparticles throughout the microgels. Representative TEM images for ULC microgels and covalent nanogold composite (cNGC) microgels are shown. Average number of nanometal particles/microgel+/−SD were also determined for at least 10 microgels/group.
Figure 3:
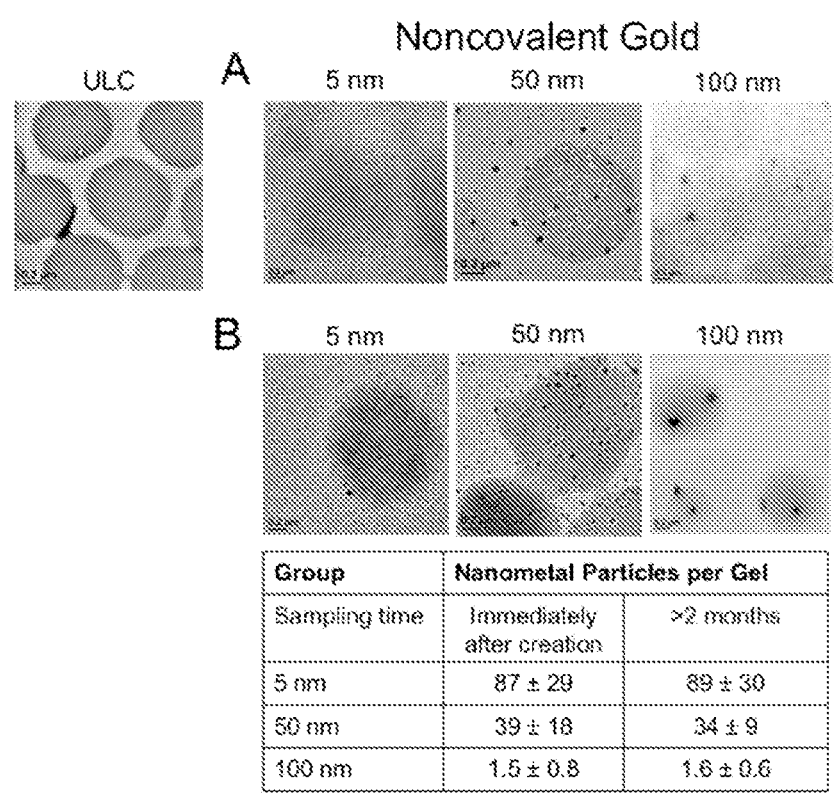
FIG. 3: Transmission Electron Microscopy demonstrated homogenous distribution of gold throughout the microgels. ncNGCs were also found to be highly stable over the course of multiple months. Representative TEM images for ULC microgels and ncNGC microgels imaged immediately after fabrication (A) and >2 months after fabrication (B) are shown. Average number of nanometal particles/microgel+/−SD were also determined for at least 10 microgels/group.

NGC size and distribution of gold nanospheres within the microgels was characterized through imaging performed on a JEOL JEM-2000FX TEM at 200 kV. TEM images reveal a homogenous distribution of gold throughout microgels for NGCs created either through noncovalent or covalent gold incorporation (FIGS. 2 and 3). Nanogold content for ncNGcs are as follows: 5 nm ncNGC composites contain 87±29 nanogold particles per microgel, 50 nm ncNGC composites contain 39±18 nanogold particles per microgel, and 100 nm ncNGC composites contain 1.5±0.8 particles per microgel. For cNGCs, nanogold content are as follows: 1× cNGCs contain 44±14 particles per microgel, 2× cNGCs contain 380±139 particles per microgel, and 3× cNGCs contain particles 677±253 per microgel. In addition, we also analyzed nanogold content for ncNGCs>2 months after fabrication. TEM images of ncNGCs show that little difference in ncNGC structure or nanogold content was observed over the course of longer storage periods (FIGS. 2 & 3), indicating that ncNGCs are relatively stable over time. Nanogold content of ncNGCs after >2 months after fabrication is as follows: 5 nm ncNGC composites contain 89±30 nanogold particles per microgel, 50 nm ncNGC composites contain 34±9 nanogold particles per microgel, and 100 nm ncNGC composites contain 1.6±0.6 particles per microgel.

Microgel deformability as a measure of the ability to spread on a glass surface, was determined with AFM using an MFP-3D BIO AFM (Asylum Research, Santa Barbara, Calif.). To prepare samples for imaging, glass coverslips were cleaned by arranging in a coverslip holder and submerging in a series of solutions in an ultrasonic bath for 10 min each: alconox detergent, water, acetone, absolute ethanol, and isopropyl alcohol. Coverslips were covered and dried. Microgel suspensions were diluted in ultrapure water and pipetted onto a coverslip and allow to dry overnight. AFM imaging was performed in tapping mode with a tip frequency of 95.4 kHz, drive amplitude of 316 mV, a set point of 500 mV, and a scan rate of 05 Hz with silicon probes (ARROW-NCR, NanoAndMore, Watsonville, Calif.). Diameter and height was determined by averaging>30 microgels in ImageJ image analysis software (National Institutes of Health, Bethesda, Md.).

Microgel morphology was characterized in situ using cryoSEM with a JEOL 7600F. Microgels suspended in water were diluted to approximately 10 μg/mL and then prepared for imaging by flash freezing in liquid nitrogen under vacuum. The samples were then fractured with a small knife and etched by warming to −95° C. for approximately 5-10 minutes. After etching, the sample is cooled to −120° C. and sputter coated with gold for 2 minutes. Imaging was performed at 50,000× magnification. As a comparison to native platelets, blood was acquired from the New York Blood Center (New York City, N.Y.) and platelets were isolated by centrifugation at 150 g's for 15 min with no deceleration to remove red blood cells and the buffy coat. Additional centrifugation of the platelet-rich plasma at 900 g for 5 minutes concentrated platelets into a pellet that was subsequently washed and resuspended in Tyrode's albumin buffer containing 0.35% human serum albumin (Fisher Scientific, Hampton, N.H.). Platelets were activated by the addition of 0.25 U/mL human α-thrombin (Enzyme Research Laboratories, South Bend, Ind.) immediately before imaging.

Figure 4:
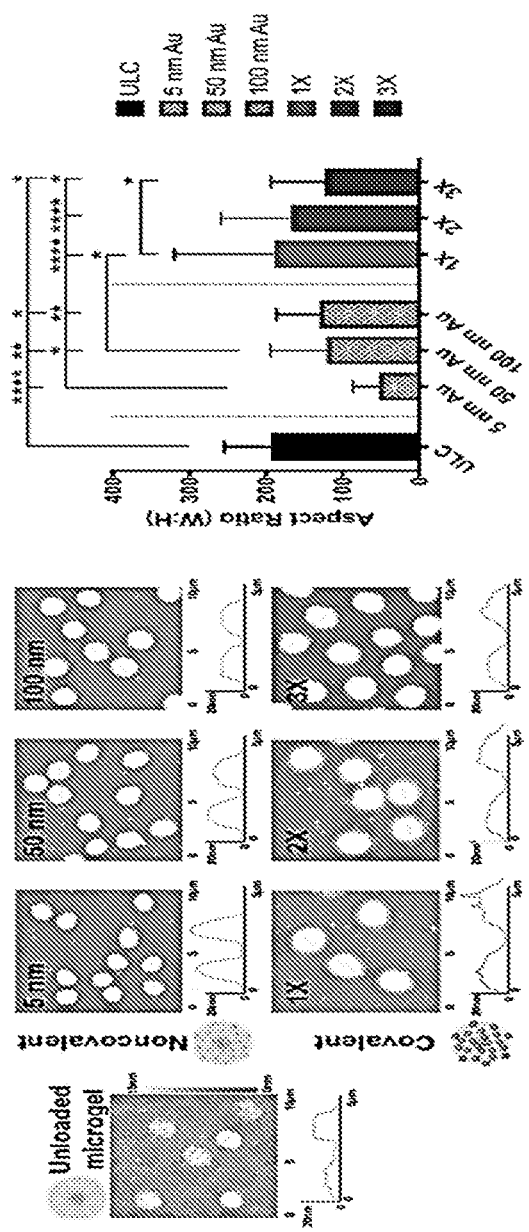
FIG. 4: AFM characterization of NGC size and spreading. Microgel size and deformability as a measure of the ability to spread on a glass surface was determined with AFM using an MFP-3D BIO AFM (Asylum Research, Santa Barbara, Calif.). Diameter and height traces were generated with Asylum AFM software for at least 30 microgels per condition from at least 3 different images. Representative images and height traces are shown. Aspect ratios (width:height) were calculated for at least 30 microgels based on the diameter and height trace measurements. $*p<0.05$; $p<0.01$; $**p<0.0001$. Noncovalent gold nanocomposite and covalent gold nanocomposite aspect ratios remained high after gold incorporation; thus deformability was maintained.

AFM Characterization (FIG. 4)

Microgel size and deformability as a measure of the ability to spread on a glass surface was determined with AFM using an MFP-3D BIO AFM (Asylum Research, Santa Barbara, Calif.). Unmodified ULC microgels had an average diameter of 1.6±0.2 μm and heights of 8.5±2.7 nm. After gold loading via the noncovalent method with either 5, 50 or 100 nm nanospheres, ncNGCs were found to have mean diameters of 1.3±0.1 μm, 1.7±0.2 μm, or 1.7±0.1 μm and mean heights of 25.0±3.5 nm, 13.7±2.5 nm, or 13.3±1.6, respectively. After gold loading via the covalent method with either 1×, 2×, or 3× gold, cNGCs were found to have mean diameters of 2.3±0.3 μm, 2.2±0.2 μm, or 2.0±0.2 μm and mean heights of 12.3±1.9 nm, 13.1±2.7 nm, or 16.0±2.2 nm, respectively. Aspect ratios (width:height) for 5, 50, and 100 nm nanosphere ncNGCs were found to be 52.7±34.0, 120.0±73.5, and 130.4±56.1, respectively, while aspect ratios for 1×, 2×, and 3× cNGCs were found to be 188.8±131.0, 168.3±90.8, and 123.8±69.7, respectively.

Figure 5:
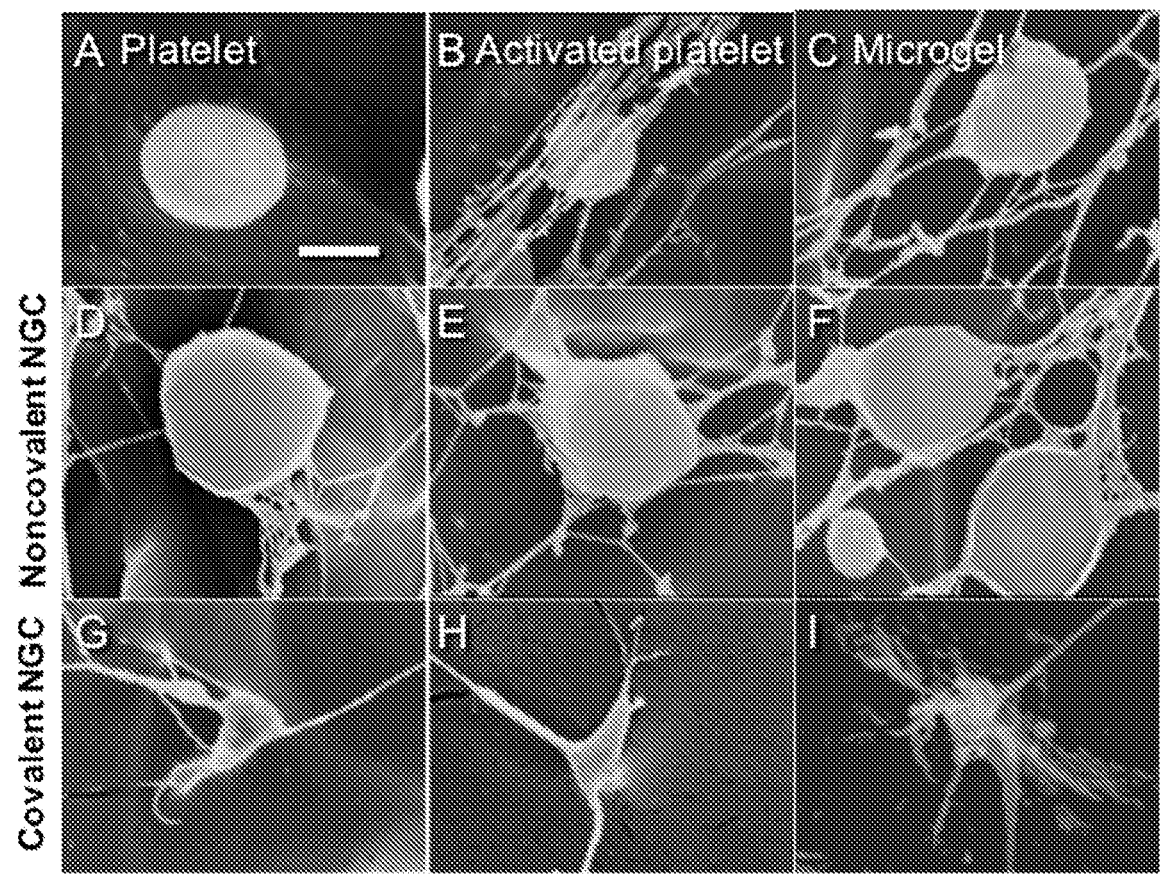
FIG. 5: CryoSEM morphology is similar to native platelets. Native circulating platelets display an ovoid morphology, A, that upon activation with 0.25 U/mL thrombin, forms spindle-like projections illustrated in B. Microgel morphology was imaged with a JEOL 7600F CryoSEM at 50000× (scale bar=500 nm) magnification. Unloaded microgels (C) illustrate a morphology similar to native platelets which remains unaffected by incorporation of gold nanospheres of varying diameters including 5 nm (D), 50 nm (E), and 100 nm (F). Covalent NGCs also display a spindle-like morphology at different synthesis formulations: 1× (G), 2× (H), and 3× (I).

CryoSEM Morphology is Similar to Native Platelets. (FIG. 5)

Native circulating platelets display an ovoid morphology, that upon activation, forms spindle-like projections. CryoSEM demonstrates the morphology change of a native platelet (A) and a platelet activated with 0.25 U/mL thrombin in B. Microgel morphology was imaged with a JEOL 7600F CryoSEM at 50000× (scale bar=500 nm) magnification. Unloaded microgels (C) illustrates a morphology similar to native platelets which remains unaffected by incorporation of gold nanospheres of varying diameters including 5 nm (D), 50 nm (E), and 100 nm (F). Covalent NGCs also display a spindle-like morphology at different synthesis formulations: 1× (G), 2× (H), and 3× (I).

Together, AFM and CryoSEM characterization demonstrate retained deformability for platelet like particles having incorporated metallic nanoparticles.

The effect of fibrin binding NGCs on clot structure was analyzed using CryoSEM. Fibrin clots were prepared with a final fibrinogen concentration (FIB 3, Enzyme Research Laboratories, South Bend, Ind.) of 2 mg/mL in HEPES buffer (25 mM HEPES, 150 mM NaCl, 5 mM CaCl$_2$). The clot was polymerized by adding 0.1 U/mL final concentration human α-thrombin (10% by volume) in the presence or absence of fibrin-binding nanogold composites (1 mg/mL of PLP). Fibrin clots were fractured, etched, and imaged via Cryo-SEM as described previously at 5,000×.

Figure 6:
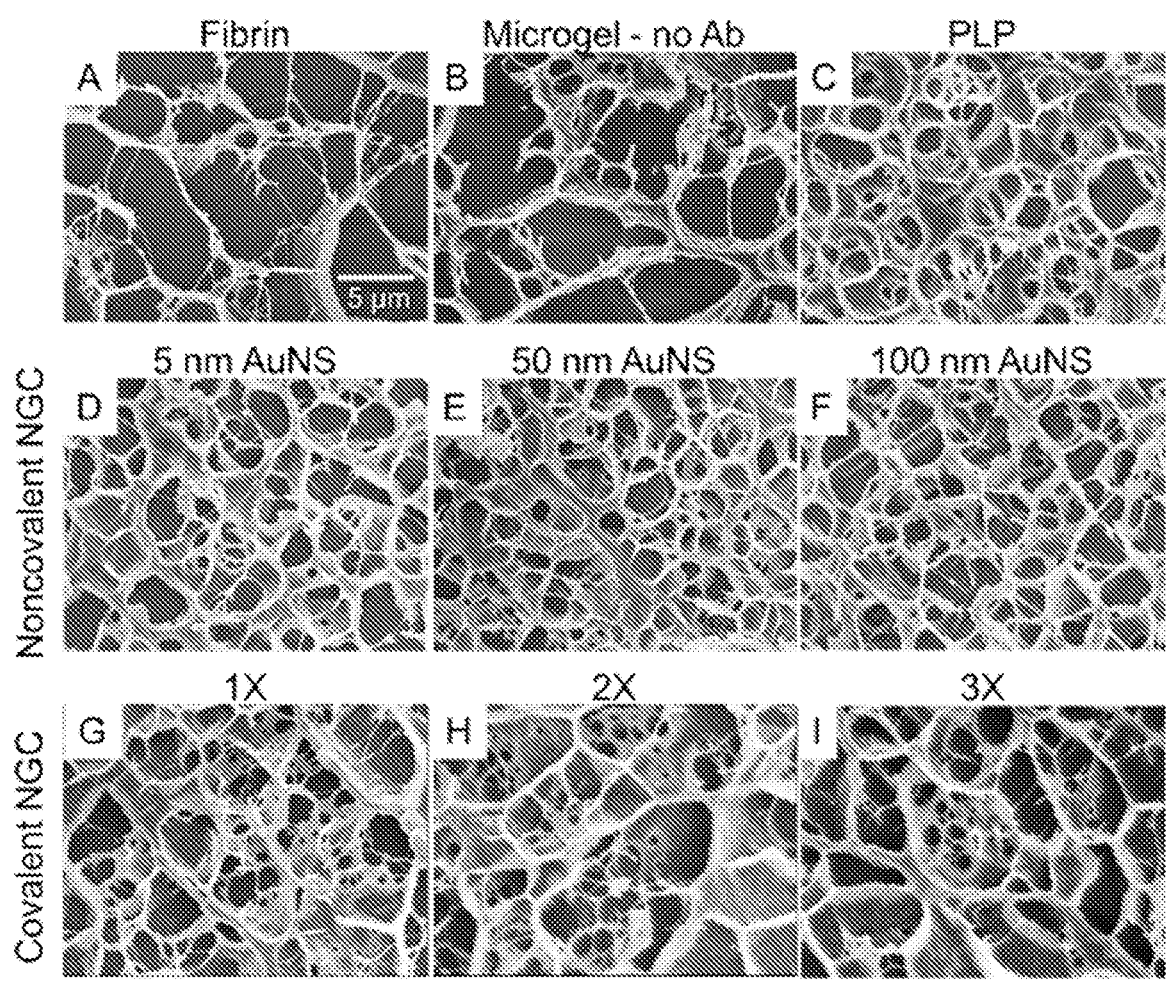
FIG. 6: CryoSEM of fibrin ultrastructure demonstrates PLP-mediated clot retraction is not affected by gold incorporation. Fibrin formed in the presence of PLPs, deformable microgels conjugated to fibrin-binding antibodies, mediated clot collapse after 24 hours (C) characterized by the increase in fibrin clot density and decrease in porosity compared to fibrin alone (A) and in the presence of non-fibrin-binding microgels (B). Noncovalent gold incorporation (D-F) did not diminish the retraction effect. Covalent gold incorporation (G-I) resulted in clot retraction but not to the same extent as noncovalent gold.

Deformable nanogold composite PLPs induce clot retraction. CryoSEM demonstrated that when both covalent and noncovalent NGCs were conjugated to fibrin-binding antibodies and polymerized into a fibrin clot, NGCs increased fibrin network density and decreased porosity compared to fibrin alone or non-binding fibrin NGCs. This fibrin clot collapse can be seen at 24 hours in the ultrastructure image of a fibrin clot at 5000× (FIG. 6). These results were similar to those observed in the presence of unmodified PLPs, seen in FIG. 6C. Because inclusion of the gold nanoparticles in the majority of the NGC microgels did not greatly influence deformability, and because particle deformability is a major feature required for induction of clot retraction by fibrin binding microgels, it is not surprising that major differences were not observed between these groups.

Figure 7:
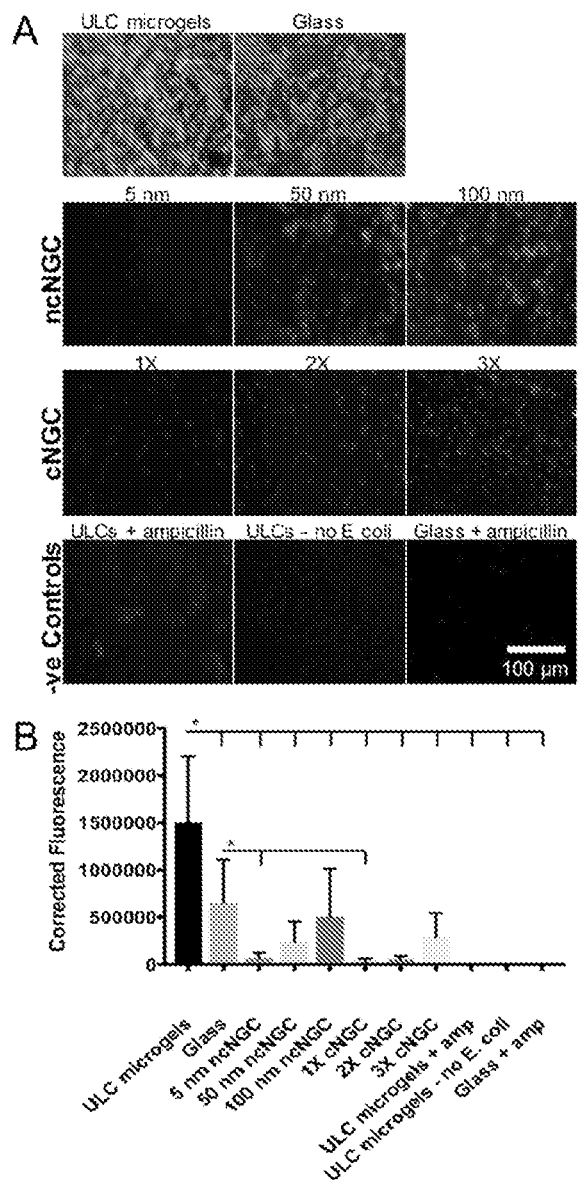
FIG. 7: NGCs inhibit bacterial growth. Microgel thin films were created on functionalized glass by actively depositing suspended ULC and NGC microgels with centrifugation (3700 g×10 min). Films were rinsed and UV sterilized before culturing with 0.5 mL of $E.$ $coli$ ($10^5$ CFU/mL) for 12 hours at 37° C. A, A modified BacLight live/dead stain was performed on washed films to observe the adhered $E.$ $coli$ (n=4). A distinct reduction in $E.$ $Coli$ growth was observed in NGC films compared to unloaded ULC microgel films demonstrated in C showing mean corrected fluorescence+/−standard deviation for a minimum of 3 images per film (n=4 films/condition) as quantified with ImageJ (Corrected Total Fluorescence=Integrated density−(Area of rect. Selection× Mean fluorescence of 2 background selections per image). Statistical analysis was performed with a one-way ANOVA and post hoc Tukey's multiple comparisons test. $*p<0.5$.

Antimicrobial susceptibility testing was performed to evaluate potential of nanogold composites as an antimicrobial agent. Microgel thin films were fabricated from ULCs, cNGCs, and ncNGCs to assess antimicrobial activity. Thin films were created on cleaned 12 nm diameter glass coverslips that were functionalized with (3-aminopropyl) trimethoxysilane (APTMS) before actively depositing microgels (1 mL of 0.5 mg/mL) Films were rinsed with water and allowed to dry overnight before UV sterilization. Gram-negative Escherichia coli (E. coli) was overlaid on each film ($10^5$ CFU/mL×0.5 mL/well in a 24-well plate) and cultured in a 37° C. humidified incubator. E. coli cultured on unmodified glass or ULC microgel thin films in the presence of 100 ug/mL ampicillin served as a control. After 12 hr, wells were rinsed and then either for a Live/Dead assay Films were incubated with a green fluorescent nucleic acid stain, 10 µM SYTO 9 dye (Thermo Fisher Scientific) and 60 µM Propidium Iodide (0.5 mL/well)×10 min at room temperature in the dark Films were washed 2× with water and mounted in BacLight mounting oil on glass slides and imaged on an EVOS FL Auto Imaging System with a 40× objective. Quantification of total corrected fluorescence was calculated for each image with ImageJ; (Corrected Total Fluorescence=Integrated density−(Area of rect. Selection× Mean fluorescence of 2 background selections per image). The corrected fluorescence intensity values shown in FIG. 7B represent green fluorescence. At least 4 films were analyzed per condition and a minimum of 3 different regions were imaged per film. Antimicrobial assays demonstrate that all formulations of NGCs inhibit bacterial growth and attachment when fabricated into thin films. A modified BacLight Live/Dead assay demonstrated significantly reduced E. coli attachment and growth on NGC thin films compared to non-gold-containing ULC microgel films (FIG. 7).

Figure 8:
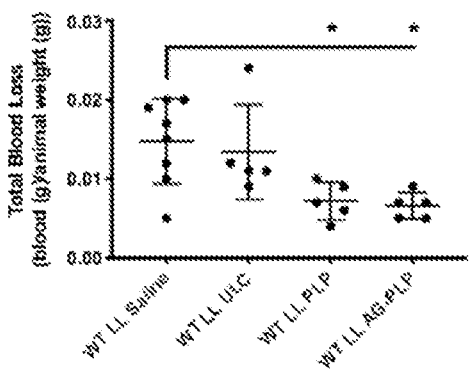
FIG. 8: Effect of nanosilver composite microgels (NSCs) on bleeding in vivo. Total blood loss in liver laceration mouse model is significantly reduced with PLP and covalent nanosilver composite PLP treatment compared to saline control. $*p<0.05$.

Evaluation of In Vivo Clotting in Rodent Models of Trauma in Presence of Nanosilver Composite Microgels (NSCs):

In vivo clotting was evaluated by evaluating bleeding following trauma in a mouse model. 8 week male c57bl/6 mice were utilized with a liver laceration injury model to determine total blood loss per animal. Animals were anesthetized with 5% isoflurane and particle treatments were injected via jugular vein. Treatments were injected with a final concentration of 10 mg particles/kg of animal in 100 µl sterile saline and were allowed to circulate in the animal's system for 5 minutes prior to liver laceration. Following laceration of the liver, blood loss was monitored for 10 minutes with blood collected by gauze at the following time points: 10 second intervals for the first 30 seconds, 30 second intervals from 1 minute to 3 minutes, and 1 minute intervals after 3 minutes until 10 minutes. Amount of blood loss was quantified by the difference in gauze weight before and after blood collection adjacent to the wound site at each time point. Heart, lungs, kidney, liver, spleen, and wound tissue were harvested for subsequent histological analysis. Treatments included ULCs, PLPs, covalent nanosilver composite PLPs (Ag-PLPs), and a saline control. We observed a significant decrease in blood loss for PLP and Ag-PLP treatment groups compared to the saline control (FIG. 8). Differences were not observed between PLP and Ag-PLP group, indicating that modification with nanosilver did not affect the hemostatic ability of the microgels.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A highly deformable microgel comprising at least one ultra-low crosslinked polymer, fibrin-binding moiety, and antimicrobial metallic nanoparticle, wherein the ultra-low crosslinked polymer comprises a polyacrylamide, a poly (acrylic acid), or a copolymer thereof, wherein the ultra-low crosslinked polymer has a crosslinking density no greater than 2.5%.

2. The microgel according to claim 1, wherein the ultra-low crosslinked polymer comprises a poly(acrylamide/acrylic acid) copolymer.

3. The microgel according to claim 1, wherein the ultra-low crosslinked polymer comprises a poly(acrylamide/acrylic acid) copolymer prepared by a precipitation polymerization of a mixture of an acrylamide monomer and an acrylic acid monomer, in which the mixture comprises no more than 20% by weight acrylic acid monomers.

4. The microgel according to claim 1, wherein the ultra-low crosslinked polymer comprises a poly(N-isopropylacrylamide/acrylic acid) copolymer.

5. The microgel gel according claim 3, wherein the mixture further comprises a polyfunctional crosslinking agent.

6. The microgel according to claim 1, wherein the fibrin binding moiety comprises at least one fibrin-binding IgG antibody, fibrin-binding peptide (i.e. fibrin knob mimic), Fragment D binding antibody; or antibody fragments that bind fibrin.

7. The microgel according to claim 1, wherein the antimicrobial metallic nanoparticles comprise gold nanoparticles, silver nanoparticles, copper nanoparticles, aluminum nanoparticles, zinc nanoparticles, or a combination thereof.

8. The microgel according to claim 1, wherein the antimicrobial metallic nanoparticles have an average particle size no greater than 1,000 nm.

9. A method of preparing the microgel according to claim 1, comprising incorporating antimicrobial metallic nanoparticles into an ultra-low crosslinked polymer, and conjugating a fibrin binding moiety to the ultra-low crosslinked polymer.

10. The method according to claim 9, wherein the antimicrobial metallic nanoparticles are incorporated prior to conjugation of the fibrin binding moiety.

11. The method according to claim 9, wherein the antimicrobial metallic nanoparticles are incorporated subsequent to conjugation of the fibrin binding moiety.

12. The method according to claim 9, wherein the antimicrobial metallic nanoparticles are incorporated by swelling an ultra-low crosslinked polymer in an aqueous composition comprising antimicrobial metallic nanoparticles.

13. The method according to claim 12, wherein the aqueous composition comprises antimicrobial metallic nanoparticles in a concentration of at least 0.01 mg/ml.

14. The method according to claim 9 wherein the nanoparticles are incorporated by reducing a metal salt in the presence of the ultra-low crosslinked polymer to incorporate antimicrobial metallic nanoparticles.

15. The method of claim 14, wherein the metal salt comprises one or more of $Au^{1+}$, $Au^{3+}$, $Ag^{1+}$, $Cu^{1+}$, $Cu^{2+}$, or $Cu^{3+}$ salts.

16. A highly deformable microgel, prepared by the process of claim 9.

17. A pharmaceutical composition comprising a highly deformable microgel comprising at least one ultra-low crosslinked polymer, fibrin-binding moiety, and antimicrobial metallic nanoparticle.

18. A method of promoting wound healing, comprising contacting a wound with the microgel according to claim 1.

19. The microgel of claim 1, having a crosslinking density no greater than 1.0%.

20. The microgel of claim 3, wherein the mixture does not contain a polyfunctional crosslinking agent.

* * * * *